(12) United States Patent
Rother et al.

(10) Patent No.: US 7,201,854 B2
(45) Date of Patent: Apr. 10, 2007

(54) ACTIVE COMPOUND COMBINATIONS FOR PROTECTING ANIMAL HIDES AND LEATHER

(75) Inventors: Heinz-Joachim Rother, Krefeld (DE); Hartmut Rehbein, Moers (DE); Martin Kugler, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/952,252

(22) Filed: Sep. 13, 2001

(65) Prior Publication Data

US 2002/0066879 A1 Jun. 6, 2002

(30) Foreign Application Priority Data

Sep. 19, 2000 (DE) ............... 100 46 265

(51) Int. Cl.
C14C 9/00 (2006.01)
C14C 1/02 (2006.01)
A01N 43/78 (2006.01)
A01N 31/16 (2006.01)
A01N 31/12 (2006.01)
A01N 41/10 (2006.01)
A01N 47/12 (2006.01)
A01N 43/80 (2006.01)
A01N 47/48 (2006.01)

(52) U.S. Cl. .................. 252/8.57; 8/94.1 R; 8/94.18; 106/15.05; 106/18.32; 106/18.35; 514/647; 514/667; 514/671; 514/672

(58) Field of Classification Search ............... 252/8.57; 8/94 R, 94.18, 94.1 R; 106/15.05, 18.32, 106/18.35; 514/646, 667, 671, 672, 647
See application file for complete search history.

(56) References Cited

U.S. PATENT DOCUMENTS

| | | | |
|---|---|---|---|
| 3,555,159 A * | 1/1971 | Feldman ............... 514/515 |
| 4,388,215 A * | 6/1983 | Ishida et al. ............ 162/160 |
| 4,803,236 A | 2/1989 | Rosenfeld ............... 524/83 |
| 4,915,943 A | 4/1990 | Gago et al. .............. 424/93 |
| 4,983,618 A * | 1/1991 | Pulido et al. ............ 514/367 |
| 5,185,357 A | 2/1993 | Inui .................. 514/372 |
| 5,244,893 A | 9/1993 | Elbe et al. ............. 514/212 |
| 5,373,016 A | 12/1994 | Brown et al. ........... 514/372 |
| 5,389,300 A * | 2/1995 | Schmitt et al. ........... 252/380 |
| 5,498,344 A | 3/1996 | Rei et al. ............. 252/404 |
| 5,629,350 A * | 5/1997 | Gartner ................ 514/736 |
| 5,888,415 A | 3/1999 | Rother et al. ............ 252/8.57 |
| 5,944,880 A | 8/1999 | Schultz et al. ........... 106/18.33 |
| 6,083,414 A * | 7/2000 | Rother et al. ........... 106/15.05 |
| 6,090,399 A | 7/2000 | Ghosh et al. ............ 424/409 |
| 6,159,999 A | 12/2000 | Uagi et al. ............. 514/372 |
| 6,217,642 B1 * | 4/2001 | Kunisch et al. .......... 106/18.33 |
| 6,375,861 B1 * | 4/2002 | Rother et al. ........... 106/15.05 |
| 6,479,521 B2 * | 11/2002 | Exner et al. ............ 514/345 |

| | | | |
|---|---|---|---|
| 2001/0027217 A1 | 10/2001 | Jaetsch et al. ............ 514/731 |
| 2002/0147227 A1 | 10/2002 | Exner et al. ............ 514/345 |
| 2003/0026833 A1 * | 2/2003 | Payne ................ 424/460 |

FOREIGN PATENT DOCUMENTS

| | | |
|---|---|---|
| DE | 137 846 | 9/1979 |
| DE | 137846 | 9/1979 |
| DE | 265 421 A1 | 3/1989 |
| DE | 265421 | 3/1989 |
| EP | 0 237 225 | 9/1987 |
| GB | 1028458 A * | 5/1966 |
| JP | 58-201864 | 11/1983 |
| JP | 60-23940 | 11/1985 |
| JP | 60-239402 A * | 11/1985 |
| JP | 4-49207 A2 * | 2/1992 |
| JP | 7247201 | 9/1995 |
| JP | 8183704 | 7/1996 |
| JP | 8277371 | 10/1996 |
| WO | 96/27483 | 12/1996 |
| WO | 98/56959 | 12/1998 |

OTHER PUBLICATIONS

Derwent Patent Abstract No. 1979-87768B, abstract of German Patent Specification No. 137846 )Sep. 1979).*
Patent Abstracts of Japan vol. 008, No. 041 (C-211), Feb. 22, 1984 & JP 58 201864 A (Pentel KK.), Nov. 24, 1983 Zusamnenfassung.
Database WPI; Derwent Publ., Ltd., London, GB; AN 1985-064786; XP002277158; "Antiseptic and antifungal agent for industrial materials-contains mixt. Of 1,2:dibromo 2,4-di:cyano-butane and 1,2-benzisothiazolin-3-one" & JP 60 019704 A (Hokko Chem Ind Co Ltd), Jan. 31, 1985.
Database WPI, Derwent Publ., Ltd., London, GB; AN 1996-482065, XP002277159, "Industrial bactericides and antiseptics for industrial use-comprises benzisothiazolin-3-one, its alkali salt and/or 3H-1,2-benzo:di:thio-3-one" & JP 08 245318 A (Daito Kagaku KK;Maruzen Yakuhin Sangyo KK;Shoei Kagaku KK), Sep. 24, 1996.
Database WPI, Derwent Publ., Ltd., London, GB; AN 1989-266922, XP002277160; "Water-colour composition for drawing with improved putrefaction resistance-contains tetra:chloromethyl:sulphonyl-pyridine antiseptic, antifungal compound, pitment, filler, water and resin" & JP 01 193372 (KSakura Kurepasu KK), Aug. 3, 1989.

(Continued)

Primary Examiner—Anthony J. Green
(74) Attorney, Agent, or Firm—Michael A. Miller

(57) ABSTRACT

The present application relates to the use of active compound combinations containing phenolic active compounds and fungicidal active compounds for preserving animal hides and leather.

11 Claims, No Drawings

OTHER PUBLICATIONS

Database WPI, Derwent Publ., Ltd., London, GB; AN 1981-76975D, XP002277161, "Antifungal Composition containing 2-n-octyl-4-isothiazolin-3-one and e.g. 2-(4-thiazolyl)benzimidazole, p-methyl phenyl iodomethyl sulphone, and 3.5-dimethyl-4-chlorophenol, used industrially" & JP 56 113706 A (Nissan Chem Ind Ltd), Sep. 7, 1981.

C. Hauber und H.-P. Germann, "Untersuchungen zum Einsatz von Konservierungsmitteln in der Chromgerbung und ihrer quantitativen Verteilung im Wet-blue.", Das Leder, Bd. 6, 1996, Seiten 189-195, XP009028834, Zusammenfassung, Seite 189, Absatz 1, Versuchsdurführung * Absatz [0008]; Abbildungen 1,2: Tabellen 1,2,4* (no month).

JALCA, vol. 94, 1999, XP009028832, Dean T. Didato et al, "Fungicides in Military Leather: An Additional Opinion for Tanners Producing Specification Leathers" (no month).

* cited by examiner

ACTIVE COMPOUND COMBINATIONS FOR PROTECTING ANIMAL HIDES AND LEATHER

BACKGROUND OF THE INVENTION

The present application relates to the use of active compound combinations containing phenolic active compounds and fungicidal active compounds for preserving animal hides and leather.

It is known that phenol derivatives and mixtures or formulations thereof can be used as compositions for the protection of materials in leather manufacture. However, it has emerged that these compounds, when employed alone or in combination, do not offer sufficient protection of stored hides and leather against microbial attack after some time.

It is furthermore known that benzimidazoles, imidazoles, triazoles, and/or morpholine derivatives in combination with phenolic compounds make possible a protection of the animal hides and leather during manufacture and storage (U.S. Pat. No. 5,888,415). The use of 2-mercapto-pyridine N-oxide and its salts for preserving leather is also known (WO 98/56959).

SUMMARY OF THE INVENTION

Surprisingly, it has now been found that combinations of certain fungicidal active compounds such as mercaptobenzothiazole, methylene bisthiocyanate, thiocyanomethylthiobenzothiazole (TCMTB), benzisothiazolinone (BIT), octylisothiazolinone (OIT), dichlorooctyl isothiazolinone (DCOIT), chlorothalonil, iodopropynyl, butylcarbamate (IPBC), di-iodo-methyl p-tolyl sulfone, N-cyclohexylbenzothiophene-2-carboxamide S,S-dioxide, and dithio-2,2'-bisbenzylmethylamide and phenolic active compounds are outstandingly suitable for the preservation of animal hides and leather.

DETAILED DESCRIPTION OF THE INVENTION

Suitable phenolic active compounds are preferably phenol derivatives such as tribromophenol, trichlorophenol, nitrophenol, 3-methyl-4-chlorophenol, 3,5-dimethyl-4-chlorophenol, phenoxyethanol, dichloro-phene, o-phenylphenol, m-phenylphenol, p-phenylphenol, 2-benzyl-4-chlorophenol (chlorophene), 2,4-dichloro-3,5-dimethylphenol, 4-chlorothymol, triclosan, fentichlor, and their ammonium, alkali metal, and alkaline earth metal salts, and mixtures thereof.

Preferred are combinations containing 3,5-dimethyl-4-chlorophenol, 2-benzyl-4-chlorophenol (BP), 3-methyl-4-chlorophenol (CMK), and/or o-phenylphenol (OPP) as phenolic constituents and one or more of the above-mentioned fungicides.

The following combinations may be mentioned in particular:
CMK/mercaptobenzothiazole,
CMK/methylene bisthiocyanate,
CMK/thiocyanomethylthiobenzothiazole (TCMTB),
CMK/benzisothiazolinone (BIT),
CMK/octylisothiazolinone (OIT),
CMK/dichlorooctylisothiazolinone (DCOIT),
CMK/iodopropynyl butylcarbamate (IPBC),
CMK/di-iodomethyl p-tolyl sulfone,
CMK/N-cyclohexylbenzothiophene-2-carboxamide S,S-dioxide,
OPP/mercaptobenzothiazole,
OPP/methylene bisthiocyanate,
OPP/thiocyanomethylthiobenzothiazole (TCMTB),
OPP/benzisothiazolinone (BIT),
OPP/octylisothiazolinone (OIT),
OPP/dichlorooctylisothiazolinone (DCOIT),
OPP/iodopropynyl butylcarbamate (IPBC),
OPP/di-iodomethyl p-tolyl sulfone,
OPP/N-cyclohexylbenzothiophene-2-carboxamide S,S-dioxide,
CMK/OPP/mercaptobenzothiazole,
CMK/OPP/methylene bisthiocyanate,
CMK/OPP/thiocyanomethylthiobenzothiazole (TCMTB),
CMK/OPP/benzisothiazolinone (BIT),
CMK/OPP/octylisothiazolinone (OIT),
CMK/OPP/dichlorooctylisothiazolinone (DCOIT),
CMK/OPP/iodopropynyl butylcarbamate (IPBC),
CMK/OPP/di-iodomethyl p-tolyl sulfone,
CMK/OPP/N-cyclohexylbenzothiophene-2-carboxamide S,S-dioxide,
CMK/BP/mercaptobenzothiazole,
CMK/BP/methylene bisthiocyanate,
CMK/BP/thiocyanomethylthiobenzothiazole (TCMTB),
CMK/BP/benzisothiazolinone (BIT),
CMK/BP/octylisothiazolinone (OIT),
CMK/BP/dichlorooctylisothiazolinone (DCOIT),
CMK/BP/iodopropynyl butylcarbamate (IPBC),
CMK/BP/di-iodomethyl p-tolyl sulfone, and
CMK/BP/N-cyclohexylbenzothiophene-2-carboxamide S,S-dioxide.

The above-mentioned fungicidal and phenolic compounds are known. See, for example, "Microbicides for the Protection of Materials", Chapmann & Hall, 1993.

In general, 5 to 200 by weight (preferably 10 to 100 by weight and especially preferably 12 to 50 parts by weight) of one or more of the above-mentioned phenolic compounds are employed per part by weight of one or more of the above-mentioned fungicides in the combinations according to the invention.

If two or more phenolic compounds are present in the combinations according to the invention, their ratio to each other can be varied within wide limits. Advantageous ratios can be determined in a simple fashion by conventional experiments that are known to the skilled worker. As a rule, the weight ratio between two phenolic compounds is between 1:1 and 1:10. If, for example, OPP is present in addition to CMK in a combination according to the invention, the preferred weight ratio OPP:CMK is between 1:1 and 1:5.

Surprisingly, the combinations according to the invention have a synergistic action, meaning that the action of the combination exceeds the action of the individual active compounds.

In general, the combinations according to the invention of the active compounds are employed as formulations. The concentration for their use is preferably 0.1 to 1% of active compound or active compound mixture based on the hides or leather to be protected.

The compositions arising from the formulation contain the active compound mixture preferably in an amount of 10 to 50%. In general, the compositions contain the following as further constituents: 0 to 30% alkali metal and/or alkaline earth metal hydroxides; 0 to 20% ionic and/or nonionic emulsifiers; 5 to 60% organic solvents such as, in particular, glycols, ketones, glycol ethers, alcohols such as ethanol, methanol, 1,2-propanediol, and n-propanol; and 0 to 0.5% of odoriferous substances and fragrances. The remainder to 100% is water or organic solvent, such as, for example, 1,2-propanediol. The percentages stated are by weight.

The active compound mixtures and the compositions that can be prepared from them are used in accordance with the invention by generally customary application methods in leather manufacture for the protection of animal hides against attack and damage by microorganisms. It is of particular interest in this context that representatives of the species *Aspergillus niger, Aspergillus repens, Hormoconis resinae, Penicillium glaucum, Trichoderma viride, Penicillium* species such as *P. citrinum* or *P. glaucum, Paecilomyces variotii, Cladosporium* species, *Mucor* species such as *Mucor mucedo, Rhizopus* species such as *Rhizopus oryzae,* and *Thizopus rouxii* are suppressed fully and permanently.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Example 1

Agar plates were inoculated with conidia of the species *Aspergillus niger, Aspergillus repens, Penicillium glaucum, Trichoderma viride,* and *Hormoconis resinae.* Wet blue samples treated with mixture I, mixture II, and mixture III were then placed on the agar plates and incubated for 28 days at 20 to 30° C. and at a relative atmospheric humidity of 95%.

Mixture I
30 parts by weight of p-chlorocresol
13 parts by weight of o-phenylphenol Mixture II
10 parts by weight of octyliso-m-thiazolinone Mixture III
30 parts by weight of p-chloro-m-cresol
10 parts by weight of 2-benzyl-4-chlorophenol
2 parts by weight of octylisothiazolinone Mold growth was observed on the test pieces after an incubation time of as little as 10 days for the wet blues preserved with mixture I and mixture II. No growth was observed after an incubation time of 20 days for mixture III.

Example 2

Formulation I
30 parts by weight of p-chloro-m-cresol
13 parts by weight of o-phenylphenol
2 parts by weight of octylisothiazolinone
12 parts by weight of naoh
14 parts by weight of 1,2-propanediol
remainder to 100 parts by weight: water Formulation II
27 parts by weight of p-chloro-m-cresol
12 parts by weight of 2-benzyl-4-chlorophenol
1 part by weight of octylisothiazolinone
Remainder to 100 parts by weight: 1,2-propanediol

What is claimed is:

1. A composition comprising:
   (1) at least one fungicidal active compound selected from the group consisting of mercaptobenzothiazole, benzisothiazolinone(BIT), octylisothiazolinone (OIT), dichlorooctylisothiazolinone (DCOIT), chlorothalonil, and 2-dithio-2,2'-bisbenzylmethylamide; and
   (2) two phenolic active compounds in a weight ratio of between 1:1 and 1:10, from 5 to 200 parts by weight of the phenolic active compounds per part by weight of the at least one fungicidal active compound, that is selected from the group consisting of nitrophenol, 3-methyl-4-chlorophenol (CMK), 3,5-dimethyl-4-chlorophenol, phenoxyethanol, dichlorophene, o-phenyl-phenol (OPP), m-phenylphenol, p-phenylphenol, 2-benzyl-4-chlorophenol (chlorophene, BP), 2,4-dichloro-3,5-dimethylphenol, 4-chlorothmol, triclosan, and fentichlor and the ammonium salts of the foregoing phenolic active compounds, alkali metal salts of the foregoing phenolic active compounds, and alkaline earth metal salts of the foregoing phenolic active compounds.

2. A composition comprising;
   (1) at least one fungicidal active compound wherein the at least one fungicidal active compound is selected from the group consisting of mercaptobenzothiazole, benzisothiazolinone (BIT), octylisothiazolinone (OIT), dichlorooctylisothiazolinone (DCOIT), di-iodomethyl p-tolyl sulfone; and
   (2) at least one phenolic active compound, from 5 to 200 parts by weight of the at least one phenolic active compound per part by weight of the at least one fungicidal active compound, wherein the phenolic active compound is 3-methyl-4-chlorophenol (CMK).

3. A composition comprising:
   (1) at least one fungicidal active compound, wherein the at least one fungicidal active compound is selected from the group consisting of mercaptobenzoth lazole, benzisothiazolinone (BIT), octylisothiazolinone (OIT), dichlorooctylisothiazolinone (DCOIT), and di-iodomethyl p-tolyl sulfone; and
   (2) least one phenolic active compound, from 5 to 200 parts by weight of the at least one phenolic active compound per part by weight of the at least one fungicidal active compound, wherein the at least one phenolic active compound comprises a mixture of 3-methyl-4-chlorophenol and o-phenylphenol (CMK/OPP).

4. A composition comprising:
   (1) at least one fungicidal active compound, wherein the at least one fungicidal active compound is selected from the group consisting of mercaptobenzothiazole, benzisothiazolinone (BIT), octylisothiazolinone (OIT), dichlorooctylisothiazolinone (DCOIT), and di-iodomethyl p-tolyl sulfone; and
   (2) at least one phenolic active compound, from 5 to 200 parts by weight of the at least one phenolic active compound per part by weight of the at least one fungicidal active compound, wherein the at least one phenolic active compound comprises a mixture of 3-methyl-4-chlorophenol and 2-benzyl-4-chlorophenol (CMK/BP).

5. A method of protecting an animal hide or leather from microbial attack comprising treating the hide or leather with a composition comprising a mixture of:
   (1) at least one fungicidal active compound selected from the group consisting of mercaptobenzothiazole, benzisothiazolinone(BIT), octylisothiazolinone (OIT), dichlorooctylisothiazolinone (DCOIT), chlorothalonil, di-iodomethyl p-tolyl sulfone, and 2-dithio-2,2'-bisbenzylmethylamide; and (2) at least one phenolic active compound, from 5 to 200 parts by weight of the at least one phenolic active compound per part by weight of the at least one fungicidal active compound, that is selected from the group consisting of nitrophenol, 3-methyl-4-chlorophenol(CMK), 3,5-dimethyl-4-chlorophenol, phenoxyethanol, dichlorophene, o-phenyl-phenol (OPP), m-phenylphenol, p-phenyiphenol, 2-benzyl-4-chlorophenol (chlorophene, BP), 2,4-dichloro-3,5-dimethylphenol, 4-chlorothymol, triclosan, fentichlor, and ammonium salts, alkali metal salts, and alkaline earth metal salts of the at least one phenolic active compound, and a combination thereof;

and thereby protecting the animal hide or leather.

6. The method of claim 5, wherein the composition is at a concentration from 0.1 to 1% based on the quantity of the animal hide or leather.

7. The method of claim 5, wherein the composition comprises two phenolic active compounds in a weight ratio of between 1:1 and 1:10.

8. The method of claim 5, wherein the at least one fungicidal active compound is selected from the group consisting of mercaptobenzothiazole, benzisothiazolinone (BIT), octylisothiazolinone (OIT), dichlorooctylisothiazolinone (DCOIT), and di-iodomethyl p-tolyl sulfone, and the at least one phenolic active compound is 3-methyl-4-chlorophenol (CMK).

9. The method of claim 5, wherein the at least one fungicidal active compound is selected from the group consisting of mercaptobenzothiazole, benzisothiazolinone (BIT), octylisothiazolinone (OIT), dichlorooctylisothiazolinone (DCOIT), and di-iodomethyl p-tolyl sulfone, and the at least one phenolic active compound is o-phenylphenol (OPP).

10. The method of claim 5, wherein the at least one fungicidal active compound is selected from the group consisting of mercaptobenzothiazole, benzisothiazolinone (BIT), octylisothiazolinone (OIT), dichlorooctylisothiazolinone (DCOIT), and di-iodomethyl p-tolyl sulfone, and the at least one phenolic active compound comprises a mixture of 3-methyl-4-chlorophenol and o-phenylphenol (CMK/OPP).

11. The method of claim 5, wherein the at least one fungicidal active compound is selected from the group consisting of mercaptobenzothiazole, benzisothiazolinone (BIT), octylisothiazolinone (OIT), dichlorooctylisothiazolinone (DCOIT), and di-iodomethyl p-tolyl sulfone, and at least one phenolic active compound comprises a mixture of 3-methyl-4-chlorophenol and 2-benzyl-4-chlorophenol (CMK/BP).

* * * * *